United States Patent

Smith

(10) Patent No.: US 8,764,261 B2
(45) Date of Patent: Jul. 1, 2014

(54) MULTI-SPOT LASER SURGICAL PROBE USING FACETED OPTICAL ELEMENTS

(75) Inventor: Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 331 days.

(21) Appl. No.: 12/959,533

(22) Filed: Dec. 3, 2010

(65) Prior Publication Data

US 2011/0141759 A1    Jun. 16, 2011

Related U.S. Application Data

(60) Provisional application No. 61/285,400, filed on Dec. 10, 2009.

(51) Int. Cl.
| | | |
|---|---|---|
| *A61B 1/06* | (2006.01) | |
| *F21S 4/00* | (2006.01) | |
| *F21V 5/00* | (2006.01) | |
| *G02B 6/06* | (2006.01) | |

(52) U.S. Cl.
USPC .......................................... 362/572; 362/555

(58) Field of Classification Search
USPC ................. 362/259, 553–555, 572–575, 804; 372/108; 606/2–3, 10–17; 607/88–89, 607/93
See application file for complete search history.

(56) References Cited

U.S. PATENT DOCUMENTS

| | | | |
|---|---|---|---|
| 4,209,017 A | 6/1980 | Shaw | |
| 4,669,818 A | 6/1987 | Myer | |
| 5,451,221 A | 9/1995 | Cho et al. | |
| 5,630,788 A * | 5/1997 | Forkner et al. | 600/182 |
| 6,011,889 A | 1/2000 | Daniel et al. | |
| 6,096,028 A | 8/2000 | Bahmanyar et al. | |
| 7,027,478 B2 | 4/2006 | Ackley | |
| 2005/0243570 A1 | 11/2005 | Chaves et al. | |
| 2006/0263034 A1 | 11/2006 | Sakurai et al. | |
| 2007/0121069 A1 | 5/2007 | Andersen et al. | |
| 2008/0086160 A1 | 4/2008 | Mastri et al. | |
| 2008/0108981 A1 | 5/2008 | Telfair et al. | |
| 2009/0190883 A1 | 7/2009 | Kato et al. | |
| 2013/0038836 A1 | 2/2013 | Smith | |

FOREIGN PATENT DOCUMENTS

| | | |
|---|---|---|
| EP | 0938871 | 9/1999 |
| WO | 2008/045316 | 4/2008 |

OTHER PUBLICATIONS

International Search Report for PCT/US2010/058942, 2 pages, Feb. 7, 2011.
Written Opinion of the International Searching Authority, International Application No. PCT/US2010/058942, Feb. 7, 2011, 6 pages.
European extended Search Report for corresponding EP Application No. EP 10836457.1 dated Jul. 16, 2013, 10 pages.

* cited by examiner

*Primary Examiner* — Jason Moon Han

(57) ABSTRACT

An optical surgical probe includes a handpiece, a light guide within the handpiece, and a multi-spot generator at a distal end of the handpiece. The handpiece is configured to optically couple to a light source. The light guide is configured to carry a light beam from the light source to a distal end of the handpiece. The multi-spot generator includes a faceted optical element with a faceted end surface spaced from a distal end of the light guide. The faceted end surface includes at least one facet oblique to a path of the light beam.

7 Claims, 2 Drawing Sheets

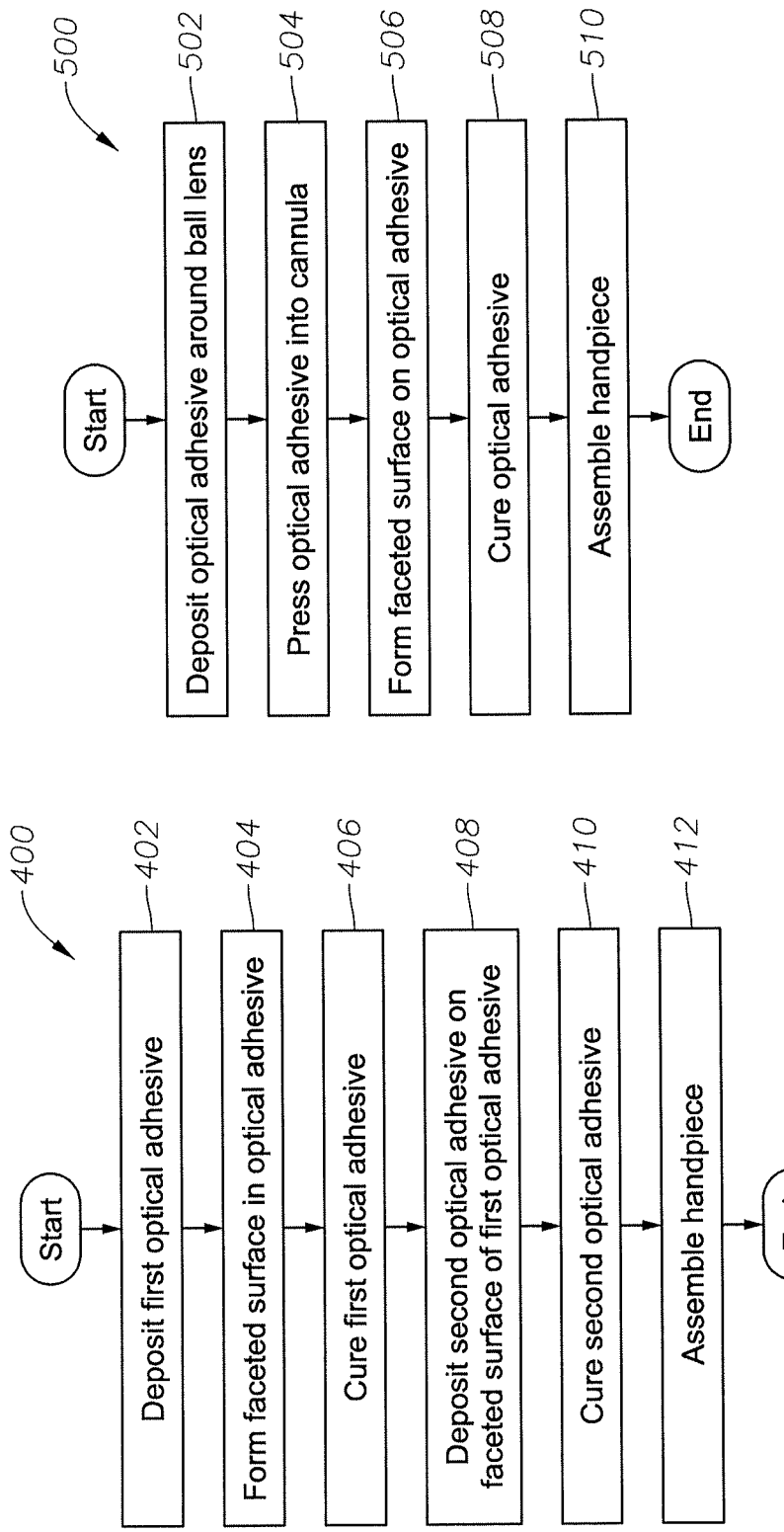

MULTI-SPOT LASER SURGICAL PROBE USING FACETED OPTICAL ELEMENTS

RELATED APPLICATIONS

This application claims priority to U.S. provisional application Ser. No. 61/285,400, filed on Dec. 10, 2009, the contents which are incorporated herein by reference.

FIELD OF THE INVENTION

This invention relates to optical surgical probes and, more particularly, to a multi-spot laser surgical probe using faceted optical elements.

BACKGROUND OF THE INVENTION

Optical surgical probes deliver light to a surgical field for a variety of applications. In some applications, it may be useful to deliver light to multiple spots in the surgical field. For example, in pan-retinal photocoagulation of retinal tissue, it may be desirable to deliver laser light to multiple spots so as to reduce the time of the pan-retinal photocoagulation procedure. Various techniques have been employed to produce multiple beams for a multi-spot pattern. For example, one approach uses diffractive elements to divide an incoming beam into multiple spots. But it is also desirable to have a multi-spot generator that can be placed at a distal end of the optical surgical probe to more easily produce multiple spots from a single input beam, so that the multi-spot generator can more easily be used with existing laser sources without the need for additional components to align the laser surgical probe with the sources.

Difficulties can arise in the use of diffractive elements at a distal end of the optical surgical probe. As one example, diffractive elements produce a multitude of higher diffraction orders, and while these orders are relatively lower in light intensity as compared to the primary spot pattern, they may not always be negligible in terms of their effects. As another example, a diffractive element may not perform identically in different refractive media. For example, if the diffractive element is placed into a medium other than air, such as saline solution or oil, spaces between the diffractive elements can be filled with material having a different refractive index than air, which can ruin the spot pattern. As yet another example, the spacing between the spots can vary for different wavelengths, which can be problematic when an aiming beam is of a certain color while a treatment beam is of a different color. Lastly, diffractive elements are frequently expensive and difficult to produce, and this is particularly the case when the diffractive element must be constructed to fit into a small area, such as a distal tip of a surgical probe for surgical instruments that are 23-gauge or smaller. Thus, there remains a need for an optical surgical probe that can produce multiple spots at a target area using optical elements at a distal end of the surgical probe.

BRIEF SUMMARY OF THE INVENTION

In particular embodiments of the present invention, an optical surgical probe includes a handpiece, a light guide within the handpiece, and a multi-spot generator at a distal end of the handpiece. The handpiece is configured to optically couple to a light source. The light guide is configured to carry a light beam from the light source to a distal end of the handpiece. The multi-spot generator includes a faceted optical element with a faceted end surface spaced from a distal end of the light guide. The faceted end surface includes at least one facet oblique to a path of the light beam. In various embodiments, the faceted end surface may be convex or concave. In certain embodiments of the present invention, the multi-spot generator further includes a focusing element, such as a gradient index (GRIN) lens or a sapphire ball lens. In certain embodiments, the faceted end surface is formed in optical adhesive, and the multi-spot generator may include multiple optical adhesive materials.

In particular embodiments of the present invention, a method of manufacturing a multi-spot optical surgical probe includes depositing an optical adhesive in a cannula for a handpiece. The handpiece for which the cannula is formed includes at least one light guide configured to carry a light beam from a light source through the handpiece. The method further includes forming the optical adhesive to produce a faceted face. The method also includes curing the optical adhesive. The method additionally includes assembling the cannula with the handpiece to form a multi-spot generator that includes the optical adhesive at a distal end of the handpiece. In various embodiments, the optical adhesive may be formed on or around a focusing element, such as a GRIN lens or a sapphire ball lens. In certain embodiments, multiple optical adhesive materials may also be used.

Other objects, features and advantages of the present invention will become apparent with reference to the drawings, and the following description of the drawings and claims.

BRIEF DESCRIPTION OF THE DRAWINGS

FIG. 4 is a flow chart illustrating an example method of manufacturing a multi-spot optical surgical probe according to a particular embodiment of the present invention; and FIG. 5 is a flow chart illustrating another example method of manufacturing a multi-spot optical surgical probe according to a particular embodiment of the present invention.

DETAILED DESCRIPTION OF THE PREFERRED EXEMPLARY EMBODIMENTS OF THE INVENTION

Figure 1:
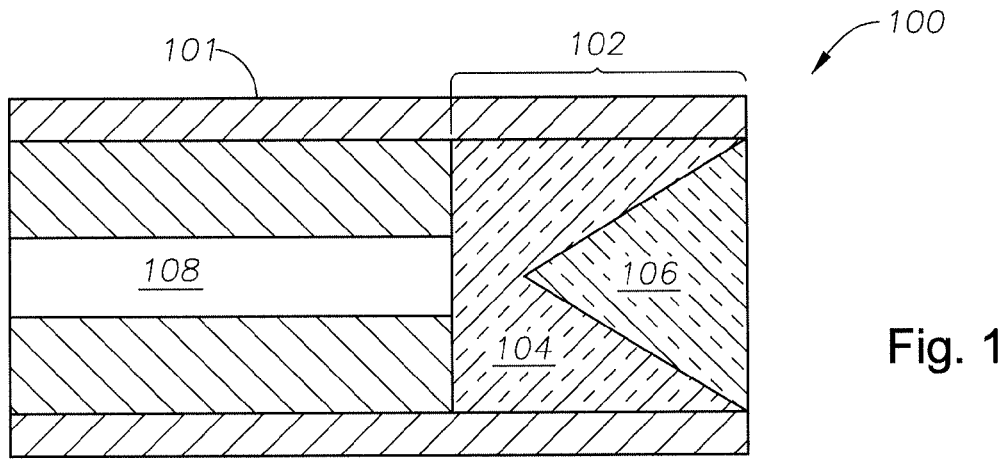
FIG. 1 illustrates a distal end of a handpiece for an optical surgical probe including a multi-spot generator according to a particular embodiment of the present invention.

FIG. 1 illustrates a distal end of a handpiece 100 for an optical surgical probe that includes a multi-spot generator 102 in a cannula 101 in accordance with a particular embodiment of the present invention, the term "distal" referring to a direction along the probe 100 toward a target area and its antonym "proximal" referring to the opposite direction. In the depicted embodiment, the multi-spot generator 102 includes a proximal faceted optical element 104 and a distal faceted optical element 106. For purposes of this specification, "faceted" refers to any optical element having an end surface formed of multiple subsurfaces (facets) so that the intersections between the facets are not smooth. The facets may be, but need not be, planar. For example, a facet may be a curved subsurface intersecting another subsurface so that the curvature is not smooth across the intersection of the subsurfaces; such embodiments may provide optical focusing power.

A light guide 108 delivers a light beam to a proximal planar face of the proximal faceted optical element 104. Although the light guide 108 could in principle be any suitable structure for transmitting light to the distal end of the handpiece 100, optical fibers are most commonly used in surgical applications. The central axis of the emitted beam from the light guide 108 is referred to as the "beam path." The light beam diverges as it travels away from the light guide 108 to a degree that depends on the numerical aperture for the light beam coupled into the light guide 108. For this reason, the faceted optical surface of faceted optical elements is spaced from a distal end of the light guide 108 so that portions of the diverging beam are refracted to different locations. In various embodiments of the invention, at least one facet is oriented such that a direction normal to a facet at a center of the facet is not parallel to the beam path of the emitted light beam. Such facets are described herein as being "oblique to the beam path."

The faceted optical elements 104 and 106 each have different refractive indices, so that as the beam exiting the light guide 108 diverges, the faceted interface between the concave faceted face of the proximal optical element 104 and the convex faceted face of the distal optical element 106 produces multiple spots emerging from a distal planar face of the distal faceted optical element 106. "Concave" and "convex" in this context refer to whether the faceted optical surface is formed inwardly or outwardly of the optical element along the beam path. Depending on the relative refractive indices of the distal faceted optical element 106 and the medium into which the surgical probe is inserted, the spots could further diverge as they pass from the distal face of the optical element 106 into the medium. In a particular example in which the surgical probe is being designed for use in saline solution, for example, the proximal faceted optical element 104 could have an index of refraction of 1.36 and the distal faceted optical element could have an index of refraction of 1.58, which can produce a spot spacing on the order of a millimeter for a target around 4 mm away, assuming an angle between the facets and the beam path is in the range of 35 to 55 degrees.

In the depicted embodiment, the optical elements 104 and 106 each have four triangular facets oblique to the beam path that meet at a point aligned with a center of the light beam from the light guide, so that the multi-spot generator 102 produces four output spots. In principle, however, the number and shape of the facets could be adjusted to produce a desired pattern of output spots. For example, the number of facets could be increased. In another example, there could be a central planar facet perpendicular to the beam path with surrounding obliquely-angled facets to produce a central spot surrounded by multiple spots.

The faceted optical elements 104 and 106 may advantageously be formed of optical adhesives. Using optical adhesives to form faceted optical elements has several technical advantages. One advantage is that the refractive index of the faceted optical elements 104 and 106 can be selected from a number of available materials. Another advantage is relative ease of forming the faceted surface as compared to harder refractive materials that may be difficult to mold, etch, cut, or machine into a suitable shape. A third advantage is that the optical adhesive material can be relatively durable in use as compared to other optical elements, like diffraction gratings, that can be relatively fragile. A fourth advantage is that the optical adhesive may be formed around other optical components, allowing the optical adhesive and the other optical components to work together in generating a multi-spot pattern.

Figure 2:
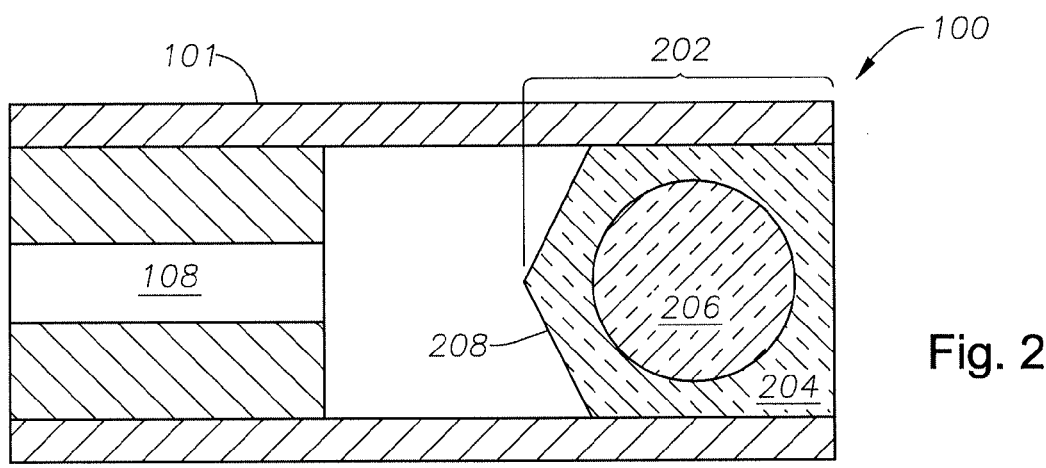
FIG. 2 illustrates another multi-spot generator according to a particular embodiment of the present invention.

As one example of how a faceted optical element can be formed around another optical component, FIG. 2 illustrates a multi-spot generator 202 according to particular embodiments of the particular invention that includes a faceted optical element 204 formed around a ball lens 206. The primary function of the ball lens 206 is to focus the incident beam so it is either collimated or converging on the distal side of the ball lens 206. The ball lens 206 may be any spherical or nearly spherical lens formed from any refractive material for transmitting light from the light source through the lens. In order to provide focusing into a collimated or converging beam, the refractive index of the ball lens should be greater than that of the surrounding adhesive medium. One example is a sapphire ball lens with a visible refractive index of roughly 1.76 and a lower adhesive refractive index of 1.57-1.58. In the depicted embodiment, a convex faceted end surface 208 of the faceted optical element 204 is arranged to point toward the light guide 108 with the faceted end surface 208 spaced from a distal end of the light guide 108. Portions of the emitted light beam are then refracted into multiple spots by the faceted optical element 204, and the spots are transmitted through the ball lens 206 out of a planar distal surface of the faceted optical element 204. In an alternative embodiment, the faceted end surface 208 could be concave. The ball lens 206 can converge the beams directed into the various spots to some degree to produce a multi-spot pattern that does not spread as rapidly when the distance from the end of the handpiece 100 increases, which in turn allows the multi-spot pattern to have a more consistent spot spacing despite slight variations in the spacing between the distal end of the handpiece 100 and the target area.

Figure 3:
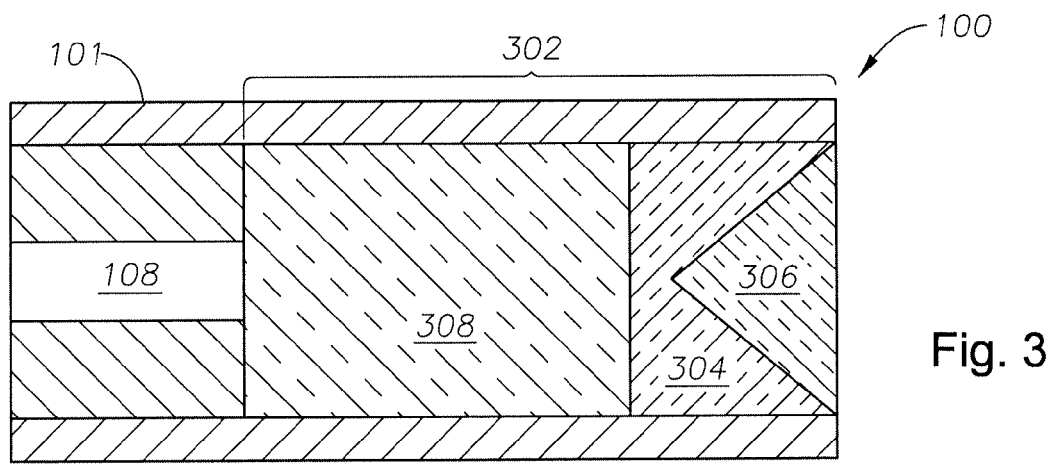
FIG. 3 illustrates yet another multi-spot generator according to a particular embodiment of the present invention.

An alternative embodiment incorporates a proximal focusing lens and a faceted surface of the faceted optical element. FIG. 3 illustrates an example of with a multi-spot generator 302 incorporating a proximal faceted optical element 304, a distal faceted optical element 306, and a cylindrical gradient index (GRIN) lens 308. The light beam emitted from the light guide 108 is expanded and then collimated or converged by the GRIN lens 308. The collimated or converged light beam then enters a planar proximal face of the proximal faceted optical element 304, and portions of the collimated or converged light beam are refracted into multiple spots as they pass through the interface between the faceted surfaces of the faceted optical elements 304 and 306. As in the previously described embodiments, this produces a multi-spot output beam emitted from a planar distal face of the distal optical element 306. Because the beam is collimated or converged by the GRIN lens, the oblique facets of the faceted optical elements 304 and 306 can be angled more shallowly with respect to the beam path as compared to the embodiment of FIG. 1, such as in a range of 15 to 35 degrees, while still producing the same degree of spread between the multiple spots at the target zone.

FIG. 4 is a flow chart 400 illustrating an example method for forming faceted optical elements from optical adhesives having different refractive indices. At step 402, a first optical adhesive is deposited within a cannula for a surgical handpiece. In a particular example, an optical fiber may be placed within the cannula using a centering cylinder during this step, and the first optical adhesive may be deposited directly onto a distal end of the optical fiber. In another example, a GRIN lens can be placed within the cannula at a distal end of the light guide, and the first optical adhesive can be deposited on a distal end of the GRIN lens. At step 404, a faceted surface is formed in the optical adhesive. For example, a pin having a convex faceted shape may be molded into the optical adhesive from a distal end of the cannula to produce a concave faceted surface in the optical adhesive. Any suitable technique for forming the optical adhesive may be used, and it may be particularly advantageous to use high-precision molding techniques to consistently and accurately produce the faceted surface of the adhesive. Then, at step 406, the first optical adhesive is cured, such as by exposure ultraviolet (UV) light, heat, or a chemical curing agent, thereby hardening the first optical adhesive in the desired shape and allowing the molding pin to be removed.

At step 408, a second optical adhesive is deposited on the distal face of the previously-cured optical adhesive. The second optical adhesive conforms to the concave faceted surface of the first optical adhesive to produce a convex faceted surface in the second optical adhesive. The distal surface of the second optical adhesive may then be flattened by pressing down a mold plate. Alternatively, the deposition of the optical adhesive can be otherwise controlled to produce a desired shape, such as by introduction into a closed mold volume. In the latter case, two faceted surfaces could be formed if desired. At step 410, the second optical adhesive is cured to harden it in the desired shape. Different curing processes may be used for the first and second optical adhesives. For example, if the adhesive is light-cured, a wavelength of light used to cure the second adhesive may be different than a wavelength used to cure the second adhesive, so that there are no negative effects from overexposure of the first adhesive to curing radiation. In another variation for light-cured adhesives, a mold plate or other closed mold used to form the second optical adhesive may also be made from a material transparent to curing radiation (e.g., quartz for UV curing radiation), so that the second adhesive may be cured with the mold plate still in place. The mold plate can then be removed after curing. The cannula with the first and second optical adhesives may then be assembled into a surgical handpiece at step 412 to complete the method.

FIG. 5 is a flow chart 500 illustrating an example method for forming a faceted optical element around another optical element in according with another embodiment of the present invention. At step 502, optical adhesive is deposited on a mold plate around a ball lens. At step 504, the optical adhesive formed around the ball lens is pressed into a distal end of a cannula. The mold plate can include a cannula guide to facilitate alignment with the cannula. As the optical adhesive is pressed into the cannula, excess optical adhesive is forced out of the cannula, so that with sufficiently careful control of the amount of deposited adhesive, a consistent and accurate amount of optical adhesive will end up within the cannula.

At step 506, a faceted surface is formed on a proximal end of the optical adhesive. The faceted surface may be convex or concave. The faceted surface may be formed, for example, by using a pin with a complementary faceted surface on the end that is inserted into a proximal end of the cannula. At step 508, the optical adhesive is cured, hardening the optical adhesive in the desired shape and allowing the molding pin and the mold plate to be removed. The handpiece is assembled with the cannula at step 510, completing the method.

The present invention is illustrated herein by example, and various modifications may be made by a person of ordinary skill in the art. Although the present invention is described in detail, it should be understood that various changes, substitutions and alterations can be made hereto without departing from the scope of the invention as claimed.

What is claimed is:

1. An optical surgical probe comprising:
   a handpiece, the handpiece configured to optically couple to a light source;
   at least one light guide within the handpiece; the at least one light guide configured to carry a light beam from the light source to a distal end of the handpiece;
   a multi-spot generator at a distal end of the handpiece, the multi-spot generator including a faceted optical element with a faceted end surface spaced from a distal end of the light guide, the faceted end surface having planar facets, making an oblique angle with a path of the light beam, wherein
   the multi-spot generator further including a spherically symmetric ball lens within the faceted optical element and is configured to split the light beam into multiple beam-components and to redirect the beam-components to multiple separate spots.

2. The optical surgical probe of claim 1, wherein the faceted optical element has a concave faceted face.

3. The optical surgical probe of claim 1, wherein the faceted optical element has a convex faceted face.

4. The optical surgical probe of claim 1, wherein the faceted optical element comprises a faceted optical adhesive.

5. The optical surgical probe of claim 1, wherein the light source comprises a laser.

6. The optical surgical probe of claim 1, wherein the handpiece is configured to switch between optical coupling to a first light source producing light of a first wavelength and optical coupling to a second light source producing light of a second wavelength different from the first wavelength, wherein at least one of the first and second wavelengths is visible.

7. The optical surgical probe of claim 1, wherein the distal end of the handpiece is sized to be 23 Gauge or smaller.

* * * * *